(12) United States Patent
Quesada Hervás (10) Patent No.: US 11,185,445 B2
(45) Date of Patent: Nov. 30, 2021

(54) PORTABLE SYSTEM THAT ALLOWS BLIND OR VISUALLY IMPAIRED PERSONS TO INTERPRET THE SURROUNDING ENVIRONMENT BY SOUND AND TOUCH

(71) Applicant: EYESYNTH, S.L., Castellón (ES)

(72) Inventor: Antonio Quesada Hervás, Castellón (ES)

( * ) Notice: Subject to any disclaimer, the term of this patent is extended or adjusted under 35 U.S.C. 154(b) by 0 days.

(21) Appl. No.: 15/578,636

(22) PCT Filed: Jun. 10, 2016

(86) PCT No.: PCT/ES2016/070441
§ 371 (c)(1),
(2) Date: Nov. 30, 2017

(87) PCT Pub. No.: WO2016/198721
PCT Pub. Date: Dec. 15, 2016

(65) Prior Publication Data
US 2018/0177640 A1    Jun. 28, 2018

(30) Foreign Application Priority Data
Jun. 12, 2015  (ES) .................. ES201530825

(51) Int. Cl.
*A61F 9/08*  (2006.01)
*G08B 3/00*  (2006.01)
(Continued)

(52) U.S. Cl.
CPC .............. *A61F 9/08* (2013.01); *G01B 11/22* (2013.01); *G06T 7/593* (2017.01); *G06T 7/90* (2017.01);
(Continued)

(58) Field of Classification Search
USPC ........................................... 348/62
See application file for complete search history.

(56) References Cited

U.S. PATENT DOCUMENTS 3,172,075 A * 3/1965 Kay .................. G01S 15/34
                                          342/24
4,292,678 A   9/1981 Kay
(Continued)

FOREIGN PATENT DOCUMENTS

| EP | 0 410 045 A1 | 1/1991 | |
| WO | WO 2013/018090 A1 | 2/2013 | |
| WO | WO-2013018090 A1 * | 2/2013 | ............... A61F 9/08 |

OTHER PUBLICATIONS

P. B. L. Meijer, "An experimental system for auditory image representations," in IEEE Transactions on Biomedical Engineering, vol. 39, No. 2, pp. 112-121, Feb. 1992. doi: 10.1109/10.121642 (Year: 1992).*

(Continued)

*Primary Examiner* — Christopher S Kelley
*Assistant Examiner* — Ana Picon-Feliciano (57) ABSTRACT

A portable system that allows blind or visually impaired persons to interpret the surrounding environment by sound or touch, said system comprising: two cameras separate from one another and configured to capture an image of the environment simultaneously, and means for generating sound and/or touch output signals. Advantageously, the system also comprises processing means connected to the cameras and to the means for generating sound and/or touch signals. The processing means are configured to combine the images captured in real time and to process the information associated with at least one vertical band with information relating to the depth of the elements in the combined image.

16 Claims, 4 Drawing Sheets

(51) Int. Cl.
  *G08B 6/00* (2006.01)
  *G01B 11/22* (2006.01)
  *G06T 7/90* (2017.01)
  *G06T 7/593* (2017.01)
  *H04N 7/18* (2006.01)

(52) U.S. Cl.
  CPC ............... *G08B 3/00* (2013.01); *G08B 6/00* (2013.01); *H04N 7/181* (2013.01); *G06T 2207/10012* (2013.01)

(56) References Cited

U.S. PATENT DOCUMENTS

| | | | |
|---|---|---|---|
| 2006/0002566 A1* | 1/2006 | Choi | H04S 1/002 381/58 |
| 2007/0016425 A1* | 1/2007 | Ward | A61H 3/061 704/271 |
| 2009/0122648 A1* | 5/2009 | Mountain | G01S 15/93 367/93 |
| 2012/0092460 A1 | 4/2012 | Mahoney | |

OTHER PUBLICATIONS

Banks, J. Bennamoun, M. and Corke, P., Non-Parametric Techniques for Fast and Robust Stereo Matching. In IEEE TENCON'97, Brisbane, Australia, Dec. 1997 (Year: 1997).*

"The vOICe at Tucson 2002," Apr. 5, 2006, http://web.archive.org/web/20060504232231/http://www.seeingwithsound.com/tucson2002.html.

Banks et al., "Non-Parametric Techniques for Fast and Robust Stereo Matching," IEEE TENCON—Speech and Image Technologies for Computing and Telecommunications, 1997, pp. 365-368.

International Search Report and Written Opinion issued in PCT/ES2016/070441 dated Jul. 26, 2016.

Kay, "Auditory perception of objects by blind persons, using a bioacoustic high resolution air sonar," J. Acoust. Soc. Am., Jun. 2000, pp. 3266-3275, vol. 107, No. 6.

Meijer, "An Experimental System for Auditory Image Representations," IEEE Transactions on Biomedical Engineering, Feb. 1992, pp. 112-121, vol. 39, No. 2.

* cited by examiner

PORTABLE SYSTEM THAT ALLOWS BLIND OR VISUALLY IMPAIRED PERSONS TO INTERPRET THE SURROUNDING ENVIRONMENT BY SOUND AND TOUCH

CROSS-REFERENCE TO RELATED APPLICATIONS

This application is a National Stage entry of International Application No.: PCT/ES2016/070441, filed Jun. 10, 2016, which claims priority to Spanish Patent Application No. P201530825, filed Jun. 12, 2015. The disclosure of the priority applications are hereby incorporated in their entirety by reference.

FIELD OF THE INVENTION

The invention relates to assistance devices for persons suffering any limitation or disability. In particular, the invention relates to an aid system primarily for blind or visually impaired persons.

PRIOR ART

Users with a visual impairment normally depend on basic aid, such as canes and guide dogs for walking around or recognizing their environment. Although systems using a higher technological level have been developed, they are often invasive and hard to handle. Also, they are usually too expensive for their use to be anything more than exclusive.

Systems today usually measure distances at one point, for example by means of using a laser, providing acoustic notification if an object is in the way. Such systems do not provide a volumetric analysis of the scene, nor does the response have nuances associated with changes in position, size or geometry (curves, edges, position with respect to the horizon line). In addition, an analysis of a scene by measuring distances with many points requires a high computing capacity, which generally renders it unfeasible for being used in real time and/or in a device that is portable.

In this context, devices for analyzing images of the environment are also known in the prior art, said devices being configured to interpret said images and mapping them out as sounds for their users, such that sound-based representations of the distance of the objects making up said images are obtained, thus integrating a three-dimensional projection that helps to orient and notify the users of possible obstacles in their way. Nevertheless, said devices are, again, ineffective as regards computing requirements, which translates in practice into a low response rate, and calculation defects causing imprecisions and an inadequate use experience for users. Examples of devices of this type based on complete mapping out of the images are the patent document ES 2133078 A1 and US 2009/122161 A1.

As an alternative to these devices, patent document ES 2517765 A1 proposes a device configured to provide a soundbank and associate each point of the images obtained with at least one sound from said soundbank, creating a map of coded sounds and representing a plane in the captured three-dimensional space. The mentioned device is also suitable for sequentially reproducing a sound from each of the points defined in the map, said sound being associated with a space represented by horizontal lines, for the purpose of making it easier to compensate for errors derived from poor placement of the device by users, for example in embodiments based on glasses, where poor horizontality can result in a defective calculation of the distances to the user.

Although the mentioned alternative allows correcting some of the deficiencies raised by earlier devices in the art, it still has the important limitation derived from the required computational resources, since although configured to represent horizontal sound patterns obtained from the images, the processing of the depths thereof is done by analyzing said images integrally, in a manner similar to that of the aforementioned systems. Accordingly, all known devices require important computational resources, greatly limiting their output and capabilities. Additionally, these devices generally require the use of inclinometers/gravimeters, making them more complex, without completely solving the problem with depth calculation precision.

Therefore, there is a need for effective systems to help persons with visual impairment that are capable of providing a comprehensible description of the environment by means of readily comprehensible audio or touch signals), and at the same time show a lower consumption of calculation and computational resources.

DISCLOSURE OF THE INVENTION

The present invention is primarily applicable to persons with vision problems. Nevertheless, it could be applicable in scenarios and circumstances of another type in which the sense of sight cannot be used or an alternative guidance system is required.

Assistance for persons is made easier with a description of the environment by means of an interpretation of the objects and obstacles existing around them which is transmitted through a signal, preferably a sound or touch signal (for example, a vibration transmitted through the sense of touch). Said signal is generated on the basis of stereo image processing to obtain a representation of areas with the highest color intensity, corresponding with far away regions while other areas with less color intensity are associated with nearby regions.

Therefore, one object of the invention relates to a portable system that allows a blind person to interpret the surrounding environment by sound or touch, comprising:
   two cameras separate from one another for capturing an image of the environment simultaneously,
   processing means combining both images in real time and establishing at least one vertical band with information relating to the depth of the elements in the combined image, wherein said processing means also divide the vertical band into a plurality of regions; define a sound or touch signal, for each region, according to the depth and of height thereof in the image; define a sound or touch output signal based on the sound or touch signals in each region of the vertical band;
   reproduction means for reproducing the sound or touch output signal.

In a preferred embodiment of the invention, the vertical band is in the central portion of the combined image and the user scans the environment upon moving. This operating mode of the invention will hereinafter be referred to as "scan mode".

The processing of only one vertical band of the image obtained by the cameras allows, on one hand, restricting the analysis of depths to the region of interest that is optimal for users (since it corresponds to the central point of focus), avoiding the peripheral regions providing information of less interest. By means of this optimization, the calculation requirement of the system can be substantially reduced, without negatively affecting the acquired information. This is due to the fact that a vertical line will condense the information relating to depth into the horizon, as this is the most relevant for the positioning of obstacles by the user. The information corresponding to the peripheral side vision is thereby generated with the natural movement of the head towards the sides by the user during movement, which shifts the vertical line of analysis and allows acquiring the remaining information, without the need to continuously process the complete image acquired by the cameras. A horizontal head movement of a few degrees allows naturally covering the frontal region of the user, for all horizon depths (covered by means of vertical line analysis). By means of this technical optimization, a savings calculation requirement of about 90% is estimated compared with alternatives in the prior art. Additionally, processing the vertical line versus the entire image captured by the cameras allows preventing the presence of sound contamination due to nearby peripheral objects, being present close to the user but not directly blocking the user's passage. In this sense, use of this system shares many similarities with the operating scan or probing mode by means of a cane for the blind, which allows quickly learning how to handle it.

In another preferred embodiment of the invention, a plurality of side vertical bands is established in the combined image on each side of the central vertical band, and a left side or right side sound or touch signal is defined from the regions of each left side band and of each right side band, respectively; the user can scan the environment without moving. This operating mode of the invention will hereinafter be referred to as "complete landscape mode". In said mode, the processing means are suitable for providing a simultaneous analysis of the plurality of side vertical bands, such that a segmentation region of the complete image acquired by the cameras is processed horizontally. Compared with the scan mode, the complete landscape mode involves a higher calculation requirement, but it provides more information with respect to the peripheral side regions of the user of the system. Nevertheless, the reduction in processing space to a plurality of vertical lines entails, just like in the scan mode, a considerable improvement in processing times and resource consumption versus known solutions in the prior art.

In another preferred embodiment of the invention, the operating modes of the processing means can be activated and deactivated by the user, such that the simultaneous analysis of the plurality of side vertical bands can be alternated with the analysis of a single vertical band. As a result, according to the user's location, said user can use the scan operating mode (that is, by means of processing depths in a central vertical line), which will be effective in most daily use situations, and the complete landscape mode (by means of a plurality of vertical bands) should it be necessary to provide additional information about the peripheral side regions.

In a preferred embodiment of the invention, the reproduction means reproduce in stereo, combining a left side sound or touch signal and a right side sound or touch signal.

In a preferred embodiment of the invention, the processing means define a sound or touch strength of the sound or touch signal according to the height of the region in the vertical band.

In a preferred embodiment of the invention, the processing means define a frequency of the sound or touch signal according to the depth of the region.

In a preferred embodiment of the invention, the depth of a region is determined according to the gray level on a depth map of the image of the environment.

In a preferred embodiment of the invention, the region comprises at least one pixel.

In a preferred embodiment of the invention, the system comprises a support structure to be carried by the user where the reproduction means and the two cameras can be located.

In a preferred embodiment of the invention based on a touch signal, the generation of said signal is based on an electroactive polymer (EAP) or on a membrane made of an elastomer the shape of which changes in response to voltage. Alternatively, the signal can be generated mechanically by means of a small vibration-generating motor.

In a preferred embodiment of the invention based on a sound signal, the frequency of said sound signal is chosen from within the range between 100 Hz and 18000 Hz.

In a preferred embodiment of the invention, the reproduction means are cochlear headphones. Advantageously, the ear is left free and the signal is received through bone. This means that the user can talk at the same time without interfering with the generated sound signal, or vice versa.

In a preferred embodiment of the invention, the support structure is chosen from at least glasses, a headband, neck support, pectoral support, shoulder support, or a handheld device.

In a preferred embodiment of the invention, the generated sound signal is non-verbal to prevent the user from being bombarded with constant spoken messages which, after prolonged use, can be bothersome and annoying. A non-verbal message is, furthermore, more readily recognized and can be played at the same time as performing other tasks. The invention can therefore be used without generating linguistic barriers resulting from the language.

DETAILED DISCLOSURE OF THE INVENTION

For the sake of greater clarity, an embodiment of the invention is described in a non-limiting manner in relation to the drawings and focusing on sound or touch signals.

Figure 1:
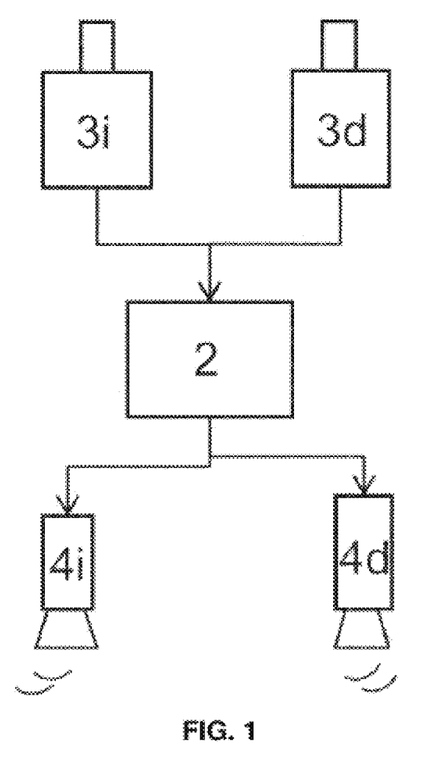
FIG. 1 shows a simplified block diagram of an embodiment of the invention.

FIG. 1 shows a block diagram with the main elements of the system of the invention. Said diagram shows how the images are acquired by means of a pair of stereo cameras (3$i$, 3$d$). They are preferably located on both sides of the face and at the height of the eyes of the user to make it easier to focus on the region of interest with head movements. The cameras (3$i$, 3$d$) are preferably aligned in parallel.

The actual circuitry of the cameras (3$i$, 3$d$) performs pre-processing on the captured image to provide a steady flow of images, preventing geometric or chromatic artifacts and aberrations. The circuitry of the sensors offers a pair of images synchronized in time.

As a result, this video stream is transmitted to a processing unit (2). The processing unit (2) is preferably a specific hardware design implementing the algorithm for converting images to audio/vibration. A cable (6) has been envisaged to communicate the cameras (3$i$, 3$d$) with the processing unit (2). Nevertheless, wireless transmission is contemplated in other more complex embodiments.

The processing unit (2) converts stereoscopic images into a grayscale depth map. A disparity map (without information about the scale) is previously generated.

Depth map is understood to be a grayscale image, in which the color called process black means maximum remoteness (depending on the scale used) and pure white means maximum closeness (depending on the scale used). The rest of the grays specify intermediate distances. Nevertheless, in other embodiments of the invention it is possible to reverse the contrast and make the darker colors correspond to the closest distances, or the use of a pre-established color scale similar to a thermographic representation.

Disparity map is understood to be the resulting image that is obtained from the superimposition of a pair of stereo images, which are subjected to mathematical processing. The binocular disparity map expresses, in one image, the differences in pixel level between two stereo images. By means of applying the mathematical disparity algorithm, by knowing the distance between cameras and the camera calibration files, the difference between pixels can be adapted to real distances. The distance of the camera from each portion (pixel size) of the image taken is known as a result of this process. A grayscale is used to express that distance.

This is then converted to a depth map. After a mathematical process in which grayscale distances/level are applied, a depth map is obtained.

Based on the generated depth map, a conversion algorithm developed for that purpose is applied, being a high optimization algorithm, and therefore, one requiring fewer computational resources, which allows special data relating to depth to be converted into audio in a more efficient manner than in the systems known.

The result is that with an initial pair of stereo images, a non-verbal stereo sound signal is achieved which is transmitted to the user through cochlear headphones or through bone conduction (4i, 4d). Audiovisual language which reliably translates visual information into auditory information in an intuitive manner for the user is thereby defined.

Figure 2:
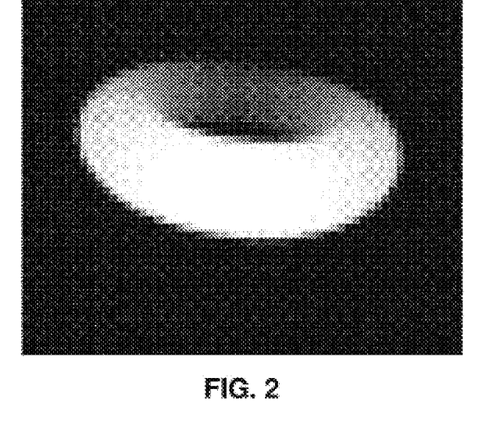
FIG. 2 shows the pixelated image of a torus analyzed by the invention.

FIG. 2 shows an example of a low-resolution depth map of a torus. Each pixel of the depth map has an associated coordinate (X, Y) corresponding with the pixel positions captured by the cameras. Furthermore, each pixel has an associated gray level (G) providing information relating to depth, i.e., the distance at which the region associated with said pixel is located.

Figure 3:
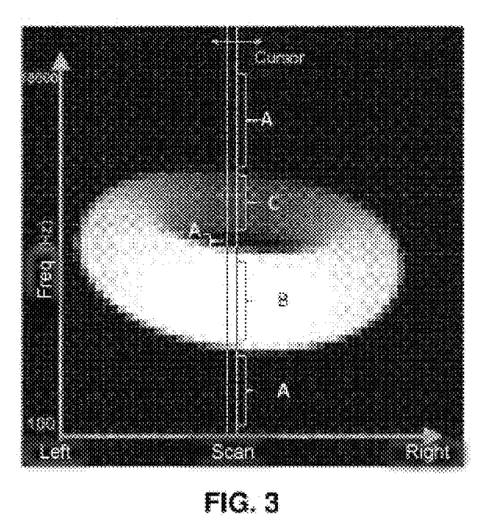
FIG. 3 shows a pixelated and processed image of the torus of FIG. 2.

FIG. 3 illustrates in a simplified manner a division of the central vertical band or column into three areas according to the gray level thereof. Area "A" is black, area "B" is white and area "C" is gray. Therefore, three different strength values are associated with each area (silence for area "A", maximum volume for area "B" and an intermediate sound intensity for area "C"). It must be understood that many more ranges of gray level and therefore associated sound intensity are usually defined. The sound signal is formed by combining the individual signals corresponding to the pixels of each area.

Using the information from the depth map, a matrix or table with information relating to the environment at that time is built. This information must be converted into audio according to the following considerations:

Disparity mapping is performed with each pair of stereo frames: Given the difference between pixels of the images and using the data from the cameras (FOV, interocular distance, specific calibration), triangulations can be established, therefore pixels can be associated with distances in the real world. With this information, the image is processed to provide a depth map. It is an outline and grayscale image of the objects expressing their volumes and real distances. This therefore provides a single composite image containing spatial information relating to the scene.

Example of scan operating mode in reference to FIG. 3. To analyze the image, it is necessary to move the head from left to right as if shaking the head no. The central cursor (in red) will therefore completely scan the torus. The generated sound will be heard in the center in the stereo panorama (since it will always be the center of the line of vision). With this scan, the horizontal size of the object is bound (movement of the neck will serve as a reference) and the vertical size will be provided by the frequency range.

Complete landscape mode using FIG. 2 for the analysis. In this case, it is not necessary for the user to move the neck to interpret what is in front of said user. The right part of the torus will sound on the right in the stereo panorama. The central and left parts will sound in a similar manner. The level of aperture of the stereo panorama will indicate the horizontal size of the torus. The vertical size will be expressed by the frequency range, like in the scan mode.

Correspondence of the image with the stereo sound is as follows: Based on an image of a landscape, the sound signal corresponds to the areas it analyzes. The left area of the image will sound in the left stereo panorama. The right area will sound in the right stereo panorama. The central area will therefore sound in the center in the stereo panorama (i.e., 50% left+50% right).

The frequency range in which the frequencies specify the height factor has a value of 100 Hz to 18000 Hz, divided into equal fragments. That range has been chosen because it is broad enough to show sound in detail and narrow enough for the average person to be able to cover them without any problems (the human range of sound is from 20 Hz to 20000 Hz). The base frequency (100 Hz) is associated with the first bottom row of pixels on the display. The highest frequency (18000 Hz) is associated with the top row of pixels. The remaining frequency fragments are assigned between them. If the image had a height of 128 pixels, each row would correspond to a fragment. If the resolution is changed, the fragments will be assigned in a manner that is proportional to the height. This method serves for systems with a low computing power. If there is a raw power available in which sound synthesis is generated in real time, the frequency range will be divided by the number of pixels in height and each frequency segment will be assigned to each pixel without interpolating or averaging.

The factor of the spatial distance with respect to the user (Z axis) is associated with the volume factor generated by the algorithm, such that a black pixel will not have a perceivable volume (i.e., -infinity) and a white pixel will have the maximum volume (0 dB). This scale will be flexible and adapts to the use of different measurement ranges (40 cm, 2 m, 6 m).

The duration of the sound per pixel is directly proportional to its "presence" on the display. If a pixel is constantly white, the sound will be repeated constantly.

The analysis of the central column is only used in scan mode. In theory, a central column with a width of 1 pixel can be used. Nevertheless, for the purpose of toning down the sound and preventing artifacts, the pixel values of the three, or even five, central columns, depending on depth map resolution (which depends on the computing power) will be averaged.

A volume intensity is associated with the grayscale value of a pixel (I). Therefore, the pixel with values 0.0.0 (RGB model) corresponds with a remote region and the associated intensity is silence (I=0). A pixel with values 255.255.255 corresponds with a very close region and the volume of the signal is maximum (I=0 dB). Each pixel can thereby be viewed as a "sound unit" used to make an audio composition. The frequency sound preferably ranges from 100 Hz to 18000 Hz.

According to the operating mode, position X of the pixel could be interpreted in two ways.

Scan mode: Only those signals corresponding to the pixels in the central column will sound. The scene is scanned when the user moves the head as if shaking it no. This is similar to scanning with a cane.

Complete landscape mode: Several columns of pixels associated with the scene will sound simultaneously. Scanning is not necessary with this mode. The image is represented (or "sounded") in its entirety. For example, the further to the right the pixels are, the louder they will sound on the right in the stereo panorama. The same is true for the central and left regions.

Complete landscape mode requires a high computing power, so depending on the performance of the processing unit (2), instead of all the columns in the image sounding, it can be optimized using five columns, i.e., central, 45°, −45°, 80°, −80°. More columns can be used according to the processing power.

The position Y of the pixel (height of the object) will define how it sounds in terms of frequency: a bandpass filter (or a generated sine wave frequency, or a pre-calculated sample with a specific frequency range, alternatives according to the calculating power of the device) is used, so the pixels in the high area will sound high-pitched, and the pixels in the low area will sound low-pitched. The sound spectrum that each pixel will cover will be defined by the number of pixels Y it will have.

EXAMPLE

This example is provided to clarify how sound is generated from the depth image. It is assumed that the scan mode has been selected and that a depth image like that shown in FIG. 3, where only three levels of gray are distinguished as an approximation, has been obtained. Therefore, in the central column there are (from bottom to top): 10 black pixels, 12 white pixels, 2 black pixels, 8 gray pixels and 15 black pixels. It is assumed that a color scale is established, 0 dB being assigned to white, −30 dB being assigned to gray and −∞ dB being assigned to black.

The strength of the signal at that moment in time would be the analog mix of all the signals.

The user would notice different frequencies according to the position of the pixel in height. The pixels that are at a lower height are lower pitched, and the pixels that are at a greater height are higher pitched. The sound generated by this column can be divided into a low pitch component with a high sound intensity (area B) and a component having an intermediate sound intensity with a higher pitched frequency (area C). This signal would be generated for the two left and right channels (and would be reproduced in the headphones (4i, 4d), respectively).

When the user changes position of the cameras by turning the head, the depth image, and therefore the associated sound signal, will be modified.

Figure 4:
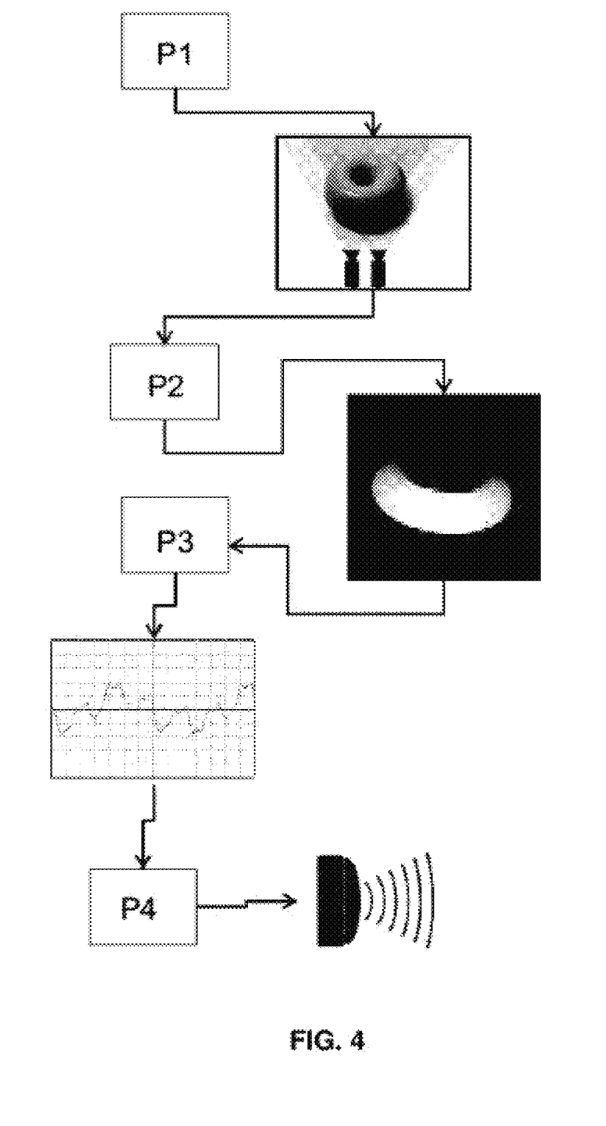
FIG. 4 shows a simplified flowchart of the method followed by the system of the invention.

FIG. 4 shows a flowchart with some of the important steps that are carried out in the scan modality. A first image capture step (P1) using the cameras (3i, 3d), a processing step (P2) to generate the depth map, an assignment step (P3) for associating frequency and sound intensity with each pixel or groups of pixels in the central column of the depth map, a generating step (P4) for generating the resulting sound signal corresponding to the central column.

Figure 5:
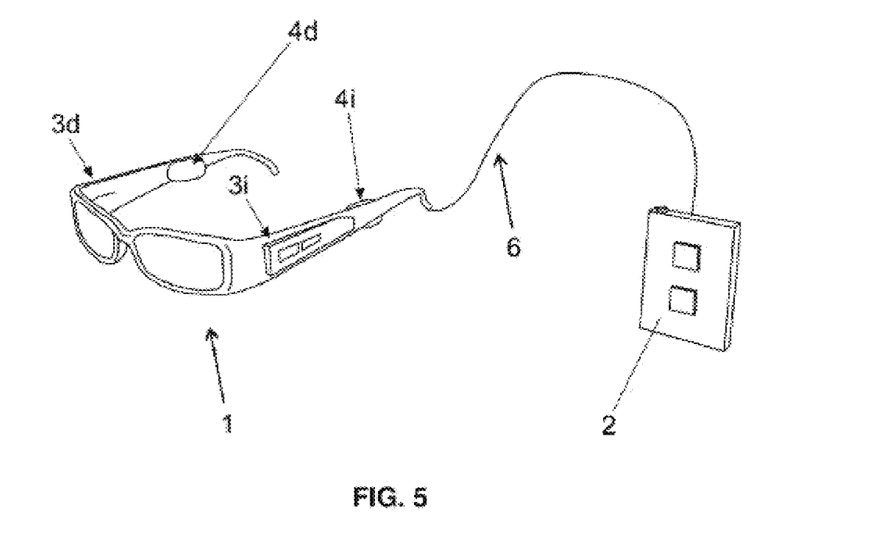
FIG. 5 shows an embodiment of the invention based on glasses.

FIG. 5 illustrates an embodiment of the invention implemented in glasses 1. Nevertheless, it can be implemented in products of another type serving as a support. For example, it can be implemented in a hat, headband, neck support, pectoral support, shoulder support, or a handheld device. The advantage of the glasses is that they are comfortable to wear and on one hand allow placing the headphones (4i, 4d) in the desired position and on the other hand they allow precise focusing of the cameras (3i, 3d) on the region of interest. The processing unit (2) is designed to be carried by the user in a pocket or on a belt. A reduction in size in the future is envisaged for the purpose of integrating it with the glasses (1). Since they are separated, a cable (6) carries the information captured by the cameras (3i, 3d) to the processing unit (2). In addition, once this information is processed, the processing unit (2) transmits the corresponding audio signals to the headphones (4i, 4d).

The amount of information and detail that the sound has allows identifying forms and spaces with a precision that was unheard of until now. In the tests conducted with the blind, it has been verified that after a short training period the present invention allows recognizing specific forms due to the associated sound. For example, bottles, glasses and plates on a table have characteristic sounds that allow distinguishing them from one another.

Cochlear headphones, which allow leaving the ear canal free, are preferably used to transmit the sound. This improves user comfort, greatly reducing listening fatigue and being much more hygienic for prolonged use sessions.

An interface associated with the processing unit (2) is envisaged in one embodiment, having a range selection button to determine the analysis distance, for example close, normal and far, with distances of 40 cm, 2 m and 6 m, respectively, or being defined by the user through an interface suited to that effect. When the button is pushed, distances will be selected in a cyclical manner. The range selection usually serves to adapt the range to different sceneries and circumstances, for example, 40 cm for locating objects on a table; 2 m for walking around the house; and 6 m for crossing the street.

In another preferred embodiment of the invention, the system comprises wireless data transmission means (for example by means of Wi-Fi, Bluetooth or other similar technologies) connected to the processing unit (2), where said transmission means are connected to an external device with a wireless connection and/or to a wearable type of device.

It is envisaged in one embodiment that the interface associated with the processing unit (2) has an analysis mode button. The selection between modes will be cyclical.

Scan mode: Analysis only in the central area of the image. The user will turn the head in a cyclical manner from left to right, scanning the scene similarly to how this would be done with a cane. The sound is monaural.

Complete landscape mode: The analysis is performed on the entire image. The sound is stereo. The user can therefore perceive forms and spaces in the entire field of vision simultaneously. For example, a column is perceived on the left (left stereo panorama), a low table is perceived in the center (central stereo panorama) and on the right (right stereo panorama) the path is clear. This prospecting mode is more complex in terms of sound since it provides more information than the scan mode does. It is easy to dominate although it does require somewhat more training.

The invention claimed is:

1. A portable system that allows blind or visually impaired persons to interpret in real time the surrounding environment by sound and touch, comprising:
  two cameras, separate from one another and configured to continuously capture images of the environment simultaneously,
  generating means for generating sound and touch output signals;
  processing means connected to the cameras and to the generating means for generating sound and touch signals,
  characterized in that said processing means are configured to combine the images captured in real time and to establish a vertical band (from the cameras' point of view) covering a total height of the combined image, and to generate sound and touch signals from pixels associated with depth information located exclusively within the vertical band, and said processing means also being configured to:
  divide the vertical band into at least two regions;
  define a sound and touch signal in each region according to the depth information of the region and the height of the region within the vertical band; and
  define a sound and touch output signal based on the sound and touch signals in each region of the vertical band.

2. The system according to claim 1, wherein the vertical band is a central band of the combined image.

3. The system according to claim 2, wherein the Processing means are configured to process a plurality of side vertical bands in the combined image, on each side-of the central vertical band, and characterized in that a left side signal and a right side signal are defined from the regions of each left side band and of each right side band, respectively.

4. The system according to claim 3, wherein the Processing means are suitable for providing a simultaneous analysis of the plurality of side vertical bands, such that a segmentation region is processed horizontally on the complete image acquired by the cameras.

5. The system according to claim 4, wherein the operating mode of the Processing means can be configured by the user, such that the mode of simultaneous analysis of the plurality of side vertical bands and mode of analysis of a single vertical band can be activated and deactivated by said user.

6. The system according to claim 1, wherein the generating means operate in stereophonic, combining a left side sound and touch signal and a right side sound and touch signal, and/or wherein the sound generated is monaural, where both modalities can be selected by the user.

7. The system according to claim 1, wherein the processing means define a strength of the sound and touch signal according to the depth of the region.

8. The system according to claim 7, wherein the processing means define a frequency of the sound and touch signal according to the height of the region in the vertical band.

9. The system according to claim 8, wherein the processing means are configured to determine the depth of a region, according to grayscale color coding or by means of a color gradient, on a depth map of the image of the environment.

10. The system according to claim 1, comprising a support structure to be carried by the user, and configured to situate the reproduction means and the two cameras.

11. The system according to claim 1, wherein the touch signal is a signal generated by vibration.

12. The system according to claim 1, wherein the frequency of the sound signal is chosen from within the range between 100 Hz and 18000 Hz.

13. The system according to claim 1, wherein the generating means comprise bone conduction headphones.

14. The system according to claim 1, wherein the support structure is chosen from at least:
  glasses,
  a headband,
  neck support,
  pectoral support,
  shoulder support,
  hand support.

15. The system according to claim 1, comprising wired, and/or wireless data transmission means connected to the processing unit, wherein said transmission means are connected to an external device with a wired, and/or wireless connection, and/or to a wearable type of device.

16. The System according to claim 1, wherein the vertical band is defined in width by at least one depth information associated pixel and in height by the total height of the combined image in depth information associated pixels.

* * * * *